PLT-348 SR
C5203 OR PP 006,181
U.S. Patent May 17, 1988 Plant 6,181
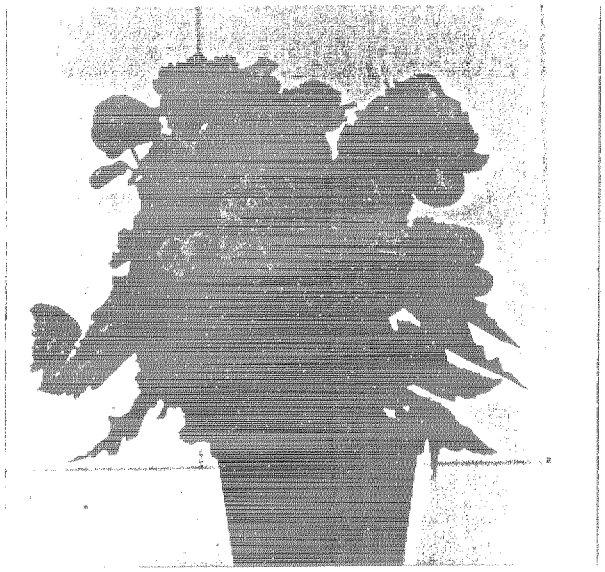

United States Patent [19]

Hvid

[11] Patent Number: Plant 6,181

[45] Date of Patent: May 17, 1988

[54] BEGONIA PLANT NAMED KATHE

[75] Inventor: Soeren Hvid, Aarup, Denmark

[73] Assignee: L. Daehnfeldt A/S, Odense, Denmark

[21] Appl. No.: 838,079

[22] Filed: Mar. 10, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Olson and Olson

[57] ABSTRACT

A new and distinctive cultivar of begonia plant bearing medium sized, heavily filled flowers of rose pink color and small, medium green, tapered leaves. The plant is characterized by rapid propagation and vigorous growth producing flowers and leaves of long persistance, excellent display, and resistance to powdery mildew.

1 Drawing Sheet

BACKGROUND OF THE INVENTION

This invention relates to a new and distinctive cultivar of begonia plant known botanically as *Begonia hiemalis* begonia (Fotsch) and known by the cultivar name Kathe.

This new cultivar was discovered by me as a mutation of Grete observed in a group of plants.

Asexual reproduction by stem and/or leaf cuttings has reproduced the unique features of the new cultivar through succescive propagations.

The following characteristics distinguish the new begonia from both its parents and other begonias commercially known and used in the floriculture industry:

(1) The new cultivar is very compact and has small medium green tapered leaves.

(2) The flowers are medium-sized and heavily filled of a nice attractive rose pink color.

(3) The cultivar propagates rapidly and uniformly by leaf cuttings.

(4) The foliage and flowers are in good proportion, presenting excellent display.

(5) The keeping qualities of the flowers and the foliage in all seasons allows production and sales efficiencies to be maximized.

(6) The new cultivar tends to be very vigorous so that 10 cm (4 inch) pot production is best done with shoot cuttings and tip pinching.

(7) Propagation by leaf cuttings is difficult under light and high temperatures in summer months. Stem cuttings can readily be produced in this season.

(8) The flower color of Kathe undergoes no or very little fading.

(9) The cultivar is compact and can be grown without growth regulators Cycocel and A-rest, but it responds well to these regulators.

THE DRAWING

The accompanying color photograph illustrates the overall appearance of this cultivar taken as a face view of the plant and showing the colors as true as it is reasonably possible to obtain in a colored reproduction of this type.

DESCRIPTION OF THE NEW VARIETY

The following is a detailed description of my new begonia cultivar based on plants produced under commercial practices in glasshouses in various places in Denmark. Color references are made to The Royal Horticultural Society Colour Chart, except where general color terms of ordinary dictionary significance are used.

Parentage: A mutation of the cultivar Grete.

Propagation:

*Type cutting.*—Tip or shoot cuttings 2-3 cm (0.75-1.25 inches) long.

*Time to root.*—27-30 days at 21° C. in summer; 30-35 days at 21° C. in winter.

*Rooting habit.*—Abundant, fibrous.

THE PLANT

Form: Low, compact, self-branching, herbaceous.

Habit of growth: Rapid, upright, strong and with short stems.

Foliage: Leaves simple, alternate, borne on vigorous petioles.

(1) *Size.*—8-10 cm (3-4 inches) long and 6-8 cm (2.4-3 inches) wide.

(2) *Shape.*—Entire, broad.

(3) *Texture.*—Firm.

(4) *Margin.*—Serrated.

(5) *Color.*—Young foliage top side; medium green; under side; light green, slightly reddening mature foliage top side; dark green under side; light green, slightly reddening.

(6) *Veination.*—Palmate.

THE FLOWER

Flowering habits: Flowering in racemes, with several clusters arising from the stem nodes at the same time giving a highly floriferous appearance. Flowering is continuous for long periods.

Natural flowering season: All seasons.

Flower bud: Flat, oval, light rose pink color.

Flowers borne: On sturdy pedicels within the form of the raceme.

Quantity: Very floriferous.

Tepals:

(1) *Shape.*—Round.

(2) *Color.*—Top side in winter when opening: medium rose pink HCC 619. fading to: rose pink HCC 619/1. under side: rose pink HCC 619/1.

(3) *Number.*—24-30.

(4) *Size.*—Basal from 35 mm (1.4 inches), interior tepals 15 mm (0.6 inches).

(5) *Flower size.*—4–6 cm (1.5–2.4 inches).

Reproductive organs:

*Stamens.*—None; cultivar is sterile.

Disease resistance:

Appears to have above average resistance to powdery mildew.

I claim:

1. A new and distinct cultivar of *Begonia hiemalis* plant named Kathe, as shown and described, and particularly characterized by its medium-sized, heavily filled rose pink flowers, fast propagation, rapid flowering and its resistance to powdery mildew.

* * * * *